United States Patent [19]

Sherwin et al.

[11] Patent Number: 4,632,120
[45] Date of Patent: Dec. 30, 1986

[54] SUBKERATINOUS ELECTROENCEPHALOGRAPHIC PROBE

[75] Inventors: Gary W. Sherwin, South Huntingdon Township, Westmoreland County; Edwin R. Mohan, Braddock Hills, both of Pa.

[73] Assignee: Westinghouse Electric Corp., Pittsburgh, Pa.

[21] Appl. No.: 727,033

[22] Filed: Apr. 25, 1985

[51] Int. Cl.⁴ .............................................. A61B 5/04
[52] U.S. Cl. .................................... 128/639; 128/731
[58] Field of Search ............... 128/639, 640, 641, 644, 128/731, 732, 733, 783, 791, 803

[56] References Cited

U.S. PATENT DOCUMENTS

| | | |
|---|---|---|
| 2,549,836 | 4/1951 | McIntyre et al. |
| 3,111,478 | 11/1963 | Watanabe ............................. 204/416 |
| 4,080,961 | 3/1978 | Eaton ................................... 128/644 |
| 4,085,739 | 4/1978 | Sams .................................... 128/644 |
| 4,120,305 | 10/1978 | Rhoads et al. ....................... 128/783 |
| 4,166,457 | 9/1979 | Jacobsen et al. .................... 128/803 |
| 4,308,873 | 1/1982 | Maynard . |
| 4,323,076 | 4/1982 | Sams .................................... 128/644 |

FOREIGN PATENT DOCUMENTS

| | | |
|---|---|---|
| 204616 | 4/1982 | Fed. Rep. of Germany ...... 128/644 |
| 676273 | 7/1979 | U.S.S.R. . |

*Primary Examiner*—William E. Kamm
*Assistant Examiner*—Randy Citrin
*Attorney, Agent, or Firm*—Daniel C. Abeles

[57] ABSTRACT

A self-preparing subkeratinous probe for electroencephalographic measurement includes a spring body which applies a penetrating force to a plow which parts hair and scrapes through a dead keratinous layer of skin to a bloodrich epidermis layer while the probe is being positioned on the head without causing bleeding. The plow includes tabs which form a gap for parting the hair and scraping the skin. The probe also includes an electrolyte tube which can be used to apply electrolyte solution to the skin and plow after it is positioned.

18 Claims, 6 Drawing Figures

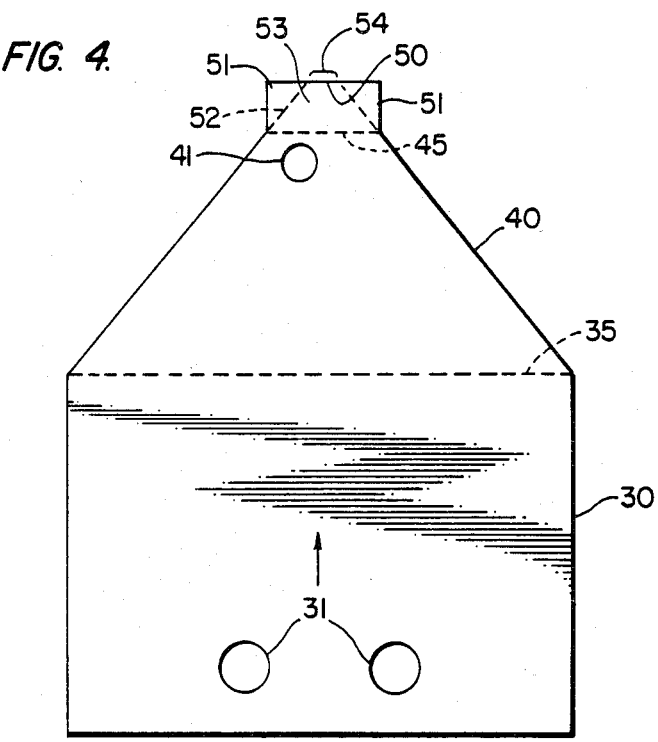
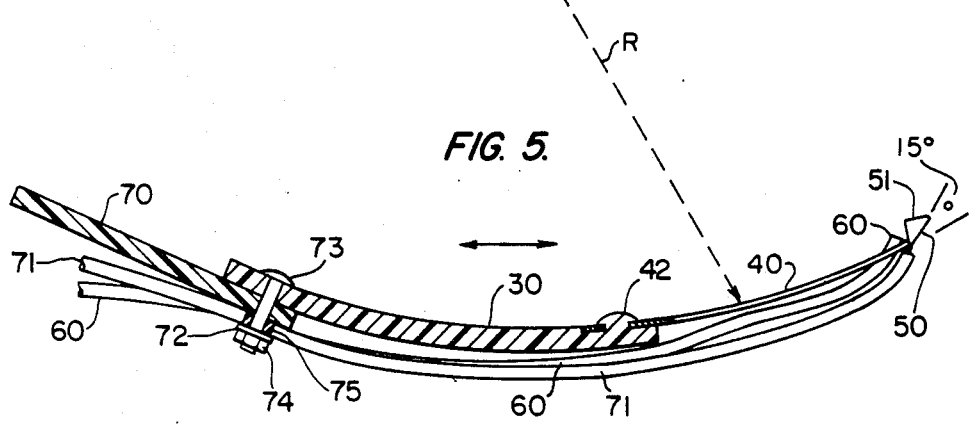

SUBKERATINOUS ELECTROENCEPHALOGRAPHIC PROBE

CROSS REFERENCE TO RELATED APPLICATIONS

This application is related to the following concurrently filed copending applications assigned to the assignee of the present invention: Electroencephalographic (EEG) Cap by Gary W. Sherwin having a U.S. Ser. No. 727,031; Low Noise EEG Probe Wiring System by Sherwin having U.S. Ser. No. 727,060; Narrow Band EEG Amplifier by Sherwin and Zomp having U.S. Ser. No. 727,056; and Evoked Potential Autorefractometry System by Bernard, Roth, Mohan, Sherwin and Zomp, having U.S. Ser. No. 727,032.

BACKGROUND OF THE INVENTION

1. Field of the Invention

The present invention is directed to a subkerationous electroencephalographic (EEG) probe and, more particularly, to a self-preparing probe which penetrates an electrically insulating keratinous cuticle layer or dead layer of skin and contacts the blood rich epidermis layer under the keratinous layer and which is useful in an evoked potential autorefractometry system for prescribing eyeglass lenses.

2. Description of the Related Art

Prior art EEG electrodes are not self-preparing electrodes in that hair, along with the electrically insulating keratinous layer of skin, must be removed before application of the electrode by shaving the hair and abrading the skin until it is raw with an abrading tool or an electrolyte cream which includes an abrading grit. FIG. 1 is an example of a prior art stick-on EEG electrode 10 which includes an adhesive 11 for sticking an insulating plastic body 12 to the skin and which can be obtained from Beckman Instruments, Shiller Park, Ill. The insulating plastic body 12 has included therein a metal conductor or slug which forms a cavity 14. The cavity 14 is filled with electrolyte cream after the skin has been abraded and before application of the electrode to the skin. A wire 15 connects the metal conductor 13 to the measurement apparatus. FIG. 2 is another example of a prior art electrode 20 which is attached to a piece of flexible cap fabric 21 by a press-fit gromet 22. This electrode 20 also forms a cavity 23 using an insulating plastic body 24 and metal conductor 25. The metal conductor 25, insulating plastic body 24, fabric 21 and press-fit gromet 22 include an injection hole 26 through which a blunt syringe needle is inserted. The blunt needle is used as a scraping tool to remove the dead layer of skin and then inject an electrolyte cream into the cavity between the skin and metal conductor 25. Further details of electrode 20 and the cap fabric 21 to which it is attached can be found in U.S. Pat. Nos. 4,323,076 and 4,085,739.

As discussed above, the prior art electrodes are non-self-preparing electrodes requiring that the hair be cut and the skin be abraded to remove the dead layer of skin before the electrodes can be properly applied. As a result, the prior art electrodes are not desirable in commercial applications where the patient visits the establishment only for a short time.

SUMMARY OF THE INVENTION

An object of the present invention is to provide a self-preparing electrode that does not require skin abrasion prior to application.

Another object of the present invention is to provide a self-preparing electrode that does not require hair cutting.

A further object of the present invention is to provide an electrode that scrapes through the dead keratinous layer of skin to the bloodrich epidermis beneath.

An additional object of the present invention is to provide an electrode that is quick and efficient to apply.

Yet, another object of the present invention is to provide an electrode which is simple in construction.

Yet, a further object of the present invention is to provide an electrode which would be inoffensive to a patient and minimally intrusive to the patient.

Still another object of the present invention is to provide an electrode which is more comfortable than prior art electrodes.

The above objects can be accomplished by a probe according to the present invention provided with a spring body which urges a plow tip to part the hair and scrape through the keratinous layer of skin as the electrode is positioned on the head. The plow tip can have an electrolyte solution applied thereto after the probe is in position.

These, together with other objects and advantages, which will be subsequently apparent, reside in the details of operation of the probe as more fully hereinafter described and claimed, reference being had to the accompanying drawings forming a part hereof, wherein like reference numerals refer to like parts throughout.

BRIEF DESCRIPTION OF THE DRAWINGS

FIG. 4 is a planar view of an EEG probe according to the present invention in an unbent state;

FIG. 5 is a side view of an EEG probe according to the present invention as mounted on a headband 70.

DESCRIPTION OF THE PREFERRED EMBODIMENTS

Figure 1:
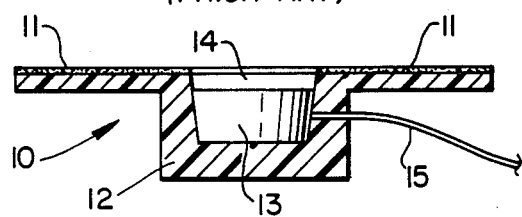
FIG. 1 is a side view of a prior art self-sticking EEG electrode 10.
Figure 2:
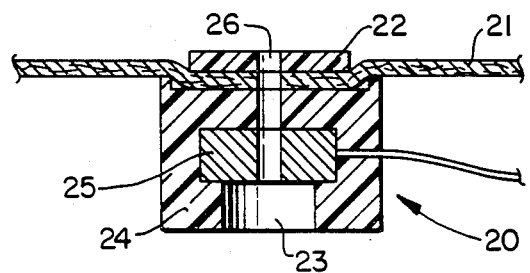
FIG. 2 is a side view of a prior art electrode 20 incorporated into a flexible EEG cap.
Figure 3:
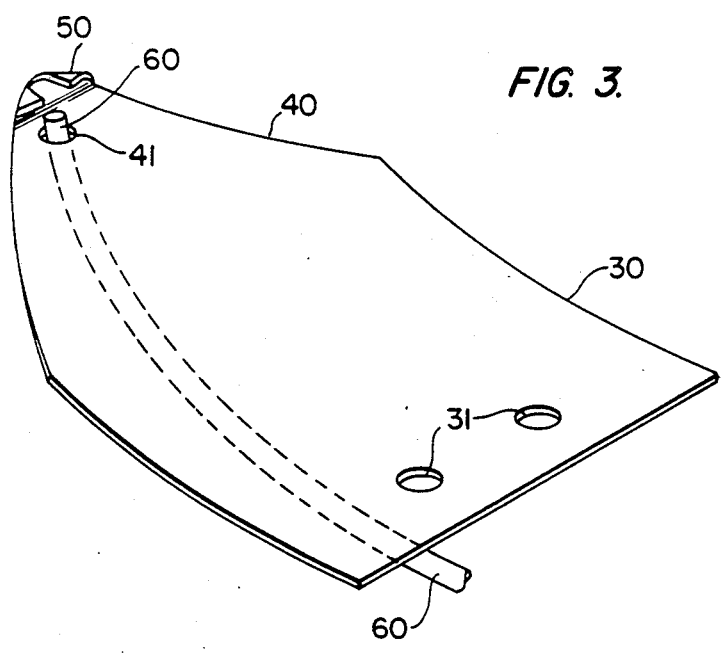
FIG. 3 is a perspective view of an EEG probe according to the present invention.

FIG. 3 is a perspective view of the probe of the present invention illustrating a spring body 30 attached to an electrode body 40 which is attached to an electrode tip or plow 50. The probe also includes electrolyte tube 60 for applying an electrolyte solution to the plow 50 after the probe is positioned. The spring body 30, electrode body 40 and plow 50 can be made of different materials. For example, the spring body 30 can be made of spring steel, plastic, coin silver or any material which maintains its spring action under bending stress and applies about two ounces of force to the plow 50. The electrode body 40 can also be made of spring steel, plastic, coin silver or any material which will not bend appreciably under normal stresses applied by the spring body 30. Plow 50 should be made of a good conductor, such as coin silver or gold and should be rigid enough not to bend under the normal stress applied by the spring body 30 and electrode body 40. A 10 mil thickness of coin silver is appropriate. As an alternative, the plow 50 can be spring steel coated wtih silver or gold thereby allowing the entire probe to be stamped from spring steel. Silver is a preferred plow 50 material or coating because many commercially available electrolyte solutions contain silver salts.

FIG. 4 is a plan view of an unbent probe in which the spring body 30 can be a square having sides of approximately an inch in length. The triangular shaped electrode body 40 can be a trapezoid approximately one-half inch in height while the plow 50 can be a square with sides approximately one-quarter inch in length. The thickness of the spring body 30, electrode body 40 and plow 50 should be such that the spring action is maintained under repeated bending cycles. The spring body 30 includes two mounting holes 31 and can be attached to the electrode body at a seam or joint 35. The electrode body 40 includes an optional electrolyte tube hole 41 and can be joined to the plow 50 by another seam 45. The seams 35 and 45 should be formed using rivets or with a crimp since heating to solder will reduce the spring action. The seams 35 and 45 also separate different materials when the spring body 30, electrode body 40 and plow 50 are made from different materials as previously discussed with respect to FIG. 3. The electrolyte hole 41 is shown offset to the side of the plow 50; however, it can be at any position near the plow 50 as long as the tube 60 will deposit electrolyte solution on the plow 50 after it is positioned against the skin. To form the plow 50, tabs 51 are bent along the bending axes 52 at an angle of approximately 90° with respect to the tip center 53. When the tabs 51 are bent, a gap 54 should be formed between the tabs 51 which allows hair to be parted by the tabs 51 as the probe is positioned. The angle of the tabs 51 with respect to the tip center 53 is not critical as long as the points of the tabs 51 will penetrate the dead layer of skin and maintain the gap 54. The arrow in the center of the spring body 30 indicates the direction of movement of the probe as it is applied to the person's head. A die stamp could be used to both cut the probe from a single piece of spring steel and bend the spring body 30, electrode body 40 and plow 50 at the appropriate angles.

FIG. 5 illustrates the relationship of a headband 70 with the spring body 30, electrode body 40 and plow 50 in an embodiment which uses different materials for the spring body 30, electrode body 40 and plow 50. The spring body 30 and electrode body 40 should form a gentle curve with a radius R of approximately 2 inches, thereby providing an angle of from 15°–20° between the axis of the headband and the end of the electrode body 40, as illustrated. The electrode body 40 could also be bent at an angle of 15°–20° with respect to the spring body 30 or electrode body 40. In any event, the bending of the various portions of the probe should position the plow 50 tips toward the skin and the spring action provided (approximately two ounces) should be sufficient to allow the dead layer of skin to be scraped away by the plow without causing bleeding. The angling of the plow 50 with respect to either the spring body 30 or electrode body 40 can be used to optimize the angle of the points formed by tabs 51 so that the penetration of the dead layer of skin is enhanced. The electrode body 40 and spring body 30 are illustrated as joined together by a plastic rivet 42 formed as an integral part of the spring body 30. During construction, the electrode body 40 is inserted on a pair of rivet shafts and the ends of the rivet 42 melted or heat fused to secure the electrode body 40 to the spring body 30. A wire 71 is soldered to the electrode body at a convenient place using an electronic solder. The wire 71 runs parallel with tube 60 through a clamp 72 which is held in place by a flat or round screw 73 and nut 74 which clamp the spring body 30 to the headband 70 while also holding the wire 71 and electrolyte tube 60 in place. The screw 73 should be rounded or flat to minimize discomfort to the patient. The clamp 72 should rigidly hold the probe to the headband 70. The tube 60 is held in place at the plow 50 by the bending of the tube 60 around the knife edge of the hole 41 in the direction of the clamp 72. The tube 60 should not be fixed to the electrode body 40 with an adhesive so that the tube 60 can be removed and cleaned when it becomes clogged. The double headed arrow in FIG. 5 illustrates the direction of movement during application of the electrode.

Figure 6:
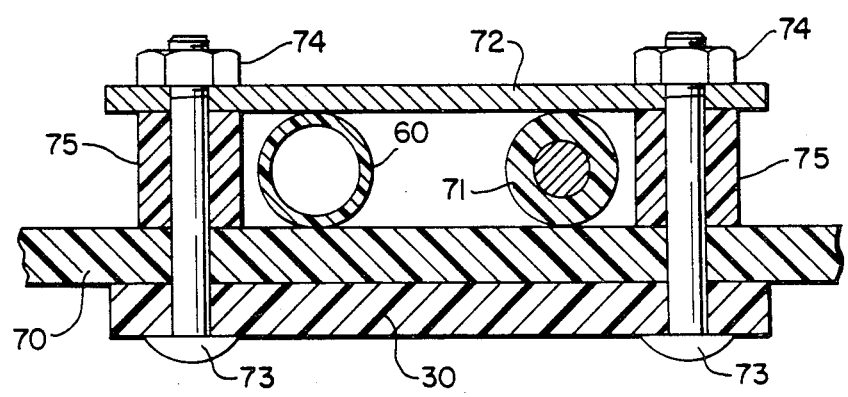
FIG. 6 is a cross-sectional view of a clamp for attaching the EEG probe according to the present invention to the headband of an EEG cap.

FIG. 6 is a cross-sectional view of the clamp 72 holding down the wire 71 and electrolyte tube 60. In order to prevent the electrolyte tube 60 and cable from being crushed, spacers 75 can be used which are slightly smaller in height than the diameter of the tube 60 and wire 71.

The probe can be mounted on the plastic bands of a relatively rigid and adjustable band in an EEG cap such as a hard hat headband or such as described in the related application mentioned previously in the cross references section. As the cap is placed upon the person's head and slid into position, the plow 50 parts the hair and scrapes through the dead caratinaceous layer of the skin. After the probe has been properly positioned, a resistive check should be conducted to ensure that the resistance is less than 5 kilohms. If the resistance is too high, a slight jiggling or rocking of the headband and, thus, the plow 50 will provide proper contact with the epidermis under the keratinous layer. If necessary, an electrolyte solution, such as saline or a commercial electrode cream, can be applied through the electrolyte tube 60 which will further increase the conduction between the probe and the epidermis. If the electrode is used with the low noise EEG probe wiring system and narrow band EEG amplifier previously mentioned in the cross references to related applications section, the resistance after probe positioning can be substantially higher than 5 kilohms.

After the probe is properly positioned, it must be held in place against the spring force provided by spring body 30 using a chin strap or heavy helmet, so that good contact is maintained with the epidermis.

Because the probe according to the present invention is self-preparing, it is particularly suitable for commercial applications in an environment such as an optician's office where an evoked potential autorefractometry system, mentioned in the cross references section, can be repeatedly used to prescribe eyeglass lenses using the potentials produced by the occipital lobes of the patient's brain. In such an environment, the probe should be cleaned after each use with alcohol using a brush or cottom swab.

The features and advantages of the invention are apparent from the details of the specification and, thus, it is intended by the appended claims to cover all such features and advantages of the probe which fall within the true spirit and scope of the invention. Further, since numerous modifications and changes will readily occur to those skilled in the art, it is not desired to limit the invention to the exact construction and materials illustrated and described and, accordingly, all suitable modifications and equivalents may be resorted to, falling within the scope of the invention. For example, if different spring body 30 materials are used, adjustments to the curvature of the spring body 30 will be required to maintain sufficient spring action to penetrate the dead layer of skin without causing bleeding and to maintain constant pressure against the scalp. Alternative electrolyte application methods are also available. For example, a rupturable plastic cell containing electrolyte could be provided to rupture through hole 41 or be punctured by the plow 50 after positioning or a blunt hypodermic needle could be used to squirt electrolyte through hole 41. In addition, the wire 71 and tube 60 can be provided with couplings and the spring body 30 could be made to snap into and out of the head band 70, thereby making the probe easily disposable.

We claim as our invention:

1. A subkeratinous electroencephalographic probe, comprising:
   electrode means for penetrating a keratinous layer of skin and contacting an epidermis as the probe is applied; and
   spring means, integral with said electrode means, for providing a penetrating force to said electrode means to penetrate the keratinous layer without penetrating the epidermis and without causing bleeding.

2. A probe as recited in claim 1, wherein said electrode means comprises a plow having bent tabs where the bent tabs produce a scraping action as said plow moves across the skin scraping through the keratinous layer.

3. A probe as recited in claim 2, wherein the bent tabs form a gap therebetween through which parted hair can pass.

4. A probe as recited in claim 2, wherein said plow has a tip center and the bent tabs are bent at an angle of approximately ninety degrees with respect to the tip center.

5. A subkaratinous electroencephalographic probe, comprising:
   electrode means for penetrating a keratinous layer of skin and contacting an epidermis as the probe is applied, said electrode means comprising:
   a plow having bent tabs where the bent tabs produce a scraping action as said plow moves across the skin scraping through the keratinous layer, said plow having a center and the bent tabs being bent at an angle of approximately ninety degrees with respect to the tip center; and
   an electrode body integral with said plow and said plow being bent at an angle of approximately 15 degrees with respect to said electrode body; and
   spring means, integral with said electrode means, for providing a penetrating force to said electrode means.

6. A probe as recited in claim 5, wherein said spring means comprises a spring body, and the electrode body and spring body form an integral curve with a radius of approximately two inches.

7. A probe as recited in claim 6, wherein said plow, said electrode body and said spring body are made from a single piece of electrically conducting material.

8. A probe as recited in claim 6, wherein said spring body is an electrically nonconductive material and said plow is an electrically conductive material.

9. A probe as recited in claim 8, wherein said electrode body is an electrically nonconductive material.

10. A probe as recited in claim 2, wherein said plow is coated with a conductive metal selected from among silver and gold.

11. A probe as recited in claim 1, further comprising electrolyte application means, attached to said electrode means, for applying an electrolyte solution to said electrode means.

12. A probe as recited in claim 11,
    wherein said electrode means comprises a plow and an electrode body, integral with said plow, having a hole, and said electrolyte application means comprises a tube, attached to said electrode body and passing through the hole in proximity to said plow, for applying the electrolyte solution to said plow.

13. A subkeratinous electroencephalographic probe, comprising a one piece electrode including a plow having bent tabs for penetrating only a keratinous layer of skin and contacting an epidermis without penetrating the epidermis, and spring means for providing a penetrating force to said plow and the bent tabs.

14. A probe as recited in claim 13, further comprising an electrolyte tube positioned adjacent said plow for applying an electrolyte solution to said plow.

15. A self-preparing subkaratinous electroencephalographic probe for mounting in an electroencephalographic cap used in an evoked potential autorefractometry system, said probe comprising:
    a plow having a tip center and bent tabs bent at an angle with respect to the tip center;
    an electrode body coupled to said plow; and
    spring means coupled to said electrode body for imparting a penetrating force to said plow tabs through said electrode body sufficient to penetrate a dead layer of skin, contacting an epidermis without penetrating the epidermis and without causing bleeding.

16. A probe as recited in claim 15, wherein said electrode body is bent with respect to said plow.

17. A probe as recited in claim 16, wherein said electrode body has a hole and said probe further comprises a tube attached to said probe and passing through the hole for application of an electrolyte solution to said plow.

18. A probe as recited in claim 17, wherein the bent tabs form a gap for parting hair.

* * * * *